United States Patent
Fiorini et al.

(10) Patent No.: US 11,266,593 B2
(45) Date of Patent: Mar. 8, 2022

(54) GARDENIA EXTRACT FOR DYEING KERATIN FIBRES

(71) Applicant: PIERRE FABRE DERMO-COSMETIQUE, Boulogne-Billancourt (FR)

(72) Inventors: Christel Fiorini, Toulouse (FR); Philippe Joulia, Villenouvelle (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 180 days.

(21) Appl. No.: 16/492,376

(22) PCT Filed: Mar. 12, 2018

(86) PCT No.: PCT/EP2018/056094
§ 371 (c)(1),
(2) Date: Sep. 9, 2019

(87) PCT Pub. No.: WO2018/162760
PCT Pub. Date: Sep. 13, 2018

(65) Prior Publication Data
US 2021/0186855 A1    Jun. 24, 2021

(30) Foreign Application Priority Data

Mar. 10, 2017 (FR) ...................... 1752005

(51) Int. Cl.
*A61Q 5/10* (2006.01)
*A61K 8/9789* (2017.01)

(52) U.S. Cl.
CPC .............. *A61K 8/9789* (2017.08); *A61Q 5/10* (2013.01); *A61K 2800/4324* (2013.01)

(58) Field of Classification Search
CPC .... A61Q 5/10; A61K 2800/4324; A61K 8/34; A61K 2800/43; A61K 8/922; A61K 2236/37; A61K 8/9789
USPC ............................................................ 8/405
See application file for complete search history.

(56) References Cited

U.S. PATENT DOCUMENTS

| 2003/0145395 A1* | 8/2003 | Murakami | A61K 8/9794 8/405 |
| 2007/0251024 A1* | 11/2007 | Greaves | A61K 8/9789 8/405 |
| 2010/0313362 A1* | 12/2010 | Vainshelboim | A61K 8/9789 8/425 |
| 2011/0154583 A1* | 6/2011 | Lewis | A61K 8/42 8/405 |

OTHER PUBLICATIONS

English transaltion of the Japanese Patent No. 2013133320 A dated Jun. 4, 2021.*

* cited by examiner

*Primary Examiner* — Eisa B Elhilo
(74) *Attorney, Agent, or Firm* — Birch, Stewart, Kolasch & Birch, LLP

(57) ABSTRACT

The present invention relates to the use of a cosmetic composition intended for dyeing keratin fibres, especially human hair, said cosmetic composition comprising as active principle a *Gardenia* extract.

10 Claims, No Drawings

GARDENIA EXTRACT FOR DYEING KERATIN FIBRES

The present invention relates to the use of a *Gardenia* extract or powder for dyeing keratin fibres, in particular hair.

Among the hair dyeing methods, mention may be of oxidative or permanent dyeing. This dyeing method employs one or more oxidative dye precursors, usually one or more oxidation bases optionally combined with one or more couplers.

These oxidation bases are colourless or slightly coloured compounds which, combined with oxidizing products, give access to, by an oxidative condensation process, coloured species which remain trapped inside the hair fibre.

During the use of an oxidative hair colouring agent, the first agent and the second agent are mixed immediately before application and the mixture is applied to the hair. During the application of the oxidative hair colouring agent, the oxidative dye having penetrated the hair is polymerized by oxidation in the hair so as to generate a bulky indoid dye and the indo dye develops. The indo dye is not easily removed from the hair because of its bulkiness, which makes it possible to ensure excellent colour retention of the dyed hair and to obtain a wide variety of colours. However, it is known that oxidative dyes can cause skin conditions. Furthermore, it has been emphasized that oxidative dyes are endocrine disruptors which negatively affect an ecosystem, and also that they can cause cancers, allergies and the like.

Coloured and colouring molecules can also be natural compounds derived from plants or trees. It is however difficult to envisage all colour shades. Consequently, there is a real need to develop hair colourings from natural substances.

Unexpectedly, the inventors have found that a *Gardenia* extract, or a *Gardenia* powder, could be useful for colouring keratin fibres, especially human.

Originating in China and Japan, *Gardenia jasminoides* J. Ellis is an evergreen shrub of the Rubiaceae family, generally about 1 to 2 m in height. This plant is cultivated in hot and humid tropical countries. The dark-green leaves are opposite, elliptic to oval-oblong, 5 to 10 cm in length and 2 to 7.5 cm in width, cuneiform at the base and acute or acuminate at the apex with a short petiole and with stipules fused in pairs. The white to ivory flowers are bell-shaped, 3 to 4 cm in size, solitary, terminal, sessile and very fragrant. The fruit is a tough, 5-sided berry, 1 to 1.5 cm in length, ovoid or ellipsoid, crowned with a persistent calyx, yellow to red at maturity and containing many seeds. The ripe fruit, harvested in the autumn and dried, is registered in the Chinese pharmacopoeia.

Chinese medicine prescribes *Gardenia* fruit in various preparations: dried fruit (Zhi-zi), fried fruit (Chaozhi-zi) or charred fruit (Jiaozhi-zi). It is prescribed for internal use as an antipyretic against bacillary dysentery, lung and urinary infections and hepatitis, or as a haemostatic in nasal haemorrhages caused by fever; and for external use to treat injuries, eye inflammation, contusions, wounds and boils. In Japanese Kampo medicine, the fruit is used to treat pain, lung disease and jaundice. These conventional uses can be explained by the pharmacological properties of the fruit, which is haemostatic, anti-inflammatory, stimulatory, cholagogic, emetic and diuretic.

The other parts of *Gardenia jasminoides* have many virtues. The antipyretic leaves are crushed in Malaysia to make poultices for treating migraines and pulmonary inflammation. The antipyretic and tonic bark is used for fever, dysentery and stomach pain. In India, the root is used for dyspepsia and nervous disorders. The emollient flowers are useful for treating ophthalmia, gonorrhoea and vaginal inflammation. The seeds are used externally in paste form to treat jaundice, rheumatism and diverticulosis.

In addition to these medicinal uses, the fruit are also used to dye foodstuffs or textiles yellow to orange owing to their high content of crocins, which are pigments identical to those of saffron.

The principal compounds of the fruit are:
- iridoids, represented chiefly by geniposide and gardenoside. The other iridoids present as well as the following compounds in smaller quantities are: 6"-O-trans-sinapoylgenipin gentiobioside, 6"-O-trans-p-coumaroylgenipin gentiobioside, 6"-O-trans-cinnamoylgenipin gentiobioside, 6"-O-trans-p-coumaroylgeniposide, 6'-O-trans-p-coumaroylgeniposide acid, 10-O-succinoylgeniposide, 6'-O-acetylgeniposide, Gardenal-I, Gardenal-II, Gardenal-III, 6-β-hydroxygeniposide, 6-α-hydroxygeniposide, 6-α-methoxygeniposide, feretoside, genipin-1-β-gentiobioside, shanzhiside, and lamalbidic and picrocrocinic acids.
- carotenoids such as croceic acid, crocetin and the crocins, glycosylated derivatives of crocetin. Crocin 1 (crocetin gentiobioside), crocin 2 (crocetin gentiobioside glucoside) and crocin 3 (crocetin glucoside) can be distinguished,
- flavonoids: gardenin, quercetin, quercetin-3-rutinoside, quercetin-3-O-glucopyranoside, isoquercitrin, corymbosin, umuhengerin, nicotiflorin.
- caffeoylquinic derivatives (3-caffeoylquinic acid, 4-caffeoylquinic acid), 3,4-dicaffeoylquinic acid, 3,5-dicaffeoylquinic acid, 4,5-dicaffeoylquinic acid, ethyl 5-O-caffeoylquinate, methyl 5-O-caffeoyl-3-O-sinapoylquinate, ethyl 5-O-caffeoyl 3-O-sinapoylquinate, methyl 5-O-caffeoyl 4-O-sinapoylquinate, ethyl 5-O-caffeoyl-4-O-sinapoylquinate, methyl 3,5-di-O-caffeoyl-4-O-(3-hydroxy-3-methyl)glutaroylquinate, 3-O-caffeoyl-4-O-sinapoylquinic acid, methyl 3-O-caffeoyl-4-O-sinapoylquinate, methyl 3-O-caffeoyl-5-O-sinapoylquinate, 3,4-di-O caffeoyl-5-O-(3-hydroxymethyl)glutaroylquinic acid, 3,5-di-O-caffeoyl-4-O-(3-hydroxymethyl)glutaroylquinic acid.
- phenolic acids such as chlorogenic, caffeic and 3,4-dihydroxy-benzoic acids.
- lignans: gardenianan A, syringaresinol, pinoresinol, syringaresinol-4-O-3-D-glucopyranoside, lariciresinol, alangilignoside D, lyoniresinol, lyoniresinol-9-O-β-D-glucopyranoside, balanophonin, glycosmisic acid, ficusal and ceplignan.
- sugars (mannitol).

The present invention relates to the use of a *Gardenia* extract or powder for dyeing keratin fibres, especially human.

According to an embodiment, the invention is thus directed at the use of a *Gardenia* extract, in particular an extract of *Gardenia* fruits, for dyeing keratin fibres, especially human keratin fibres, more particularly hair. The invention is more particularly directed at the use of a *Gardenia* extract for dyeing hair blonde. More particularly, the invention is directed at the dyeing blonde of hair which has been bleached beforehand.

According to an embodiment, the invention is thus directed at the use of a *Gardenia* powder, in particular a powder of *Gardenia* fruits, said fruits being preferably dried beforehand, for dyeing keratin fibres, especially human keratin fibres, more particularly hair. The invention is directed more particularly at the use of a *Gardenia* powder, in particular a powder of *Gardenia* fruits, in particular of dried fruits, for dyeing hair blonde. More particularly the invention is directed at the dyeing blonde of hair which has been bleached beforehand.

EMBODIMENTS OF THE INVENTION

1. Use of a *Gardenia* extract for dyeing keratin fibres, especially human keratin fibres, more particularly hair, characterized in that the extract contains between 0.1 and 10 wt % crocins, preferentially between 1 and 5 wt %, relative to the weight of the dry extract.

2. Use according to embodiment 1, characterized in that the extract is an extract of *Gardenia* fruits.

3. Use according to one of embodiments 1 to 2, characterized in that the extract is an aqueous or alcoholic or hydroalcoholic extract.

4. Use according to one of embodiments 1 to 3, characterized in that the extract is a dry extract.

5. Use according to one of embodiments 1 to 4, for dyeing hair blonde, more particularly for dyeing hair which has been bleached beforehand blonde.

6. Use of a cosmetic composition intended for dyeing keratin fibres, especially human, said cosmetic composition comprising as active principle a *Gardenia* extract as defined in one of embodiments 1 to 4.

7. Use according to embodiment 6, characterized in that the composition comprises, in addition to the *Gardenia* extract as dye active principle, a cosmetically acceptable excipient.

8. Use according to one of embodiments 6 or 7, characterized in that the composition has a pH ranging between 4 and 8.

9. Use according to one of embodiments 6 to 8, characterized in that the composition is free of reducing compound.

10. Use according to one of embodiments 6 to 9, characterized in that the composition is free of alkaline fixing compound.

11. Use of a *Gardenia* powder for dyeing keratin fibres, especially human keratin fibres, more particularly hair, characterized in that the *Gardenia* powder contains between 0.1 and 10 wt % crocins, preferentially between 1 and 5 wt %, relative to the weight of the powder.

12. Use according to embodiment 11, characterized in that the powder is a powder of *Gardenia* fruits, preferably of dried *Gardenia* fruits.

13. Use according to one of embodiments 11 to 12, for dyeing hair blonde, more particularly for dyeing hair which has been bleached beforehand blonde.

14. Use of a cosmetic composition intended for dyeing keratin fibres, especially human, said cosmetic composition comprising as active principle a *Gardenia* powder as defined in one of embodiments 11 to 12.

15. Use according to embodiment 14, characterized in that the composition comprises, in addition to the *Gardenia* powder as dye active principle, a cosmetically acceptable excipient.

16. Use according to one of embodiments 14 or 15, characterized in that the composition has a pH ranging between 4 and 8.

17. Use according to one of embodiments 14 to 16, characterized in that the composition is free of reducing compound.

18. Use according to one of embodiments 14 to 17, characterized in that the composition is free of alkaline fixing compound.

19. A kit comprising a *Gardenia* extract as defined in one of embodiments 1 to 4, a cosmetically acceptable excipient and a set of instructions, for use for dyeing hair, in particular for dyeing hair blonde.

20. A kit comprising a *Gardenia* powder as defined in one of embodiments 11 to 12, a cosmetically acceptable excipient and a set of instructions, for use for dyeing hair, in particular for dyeing hair blonde.

21. A cosmetic treatment method intended for dyeing keratin fibres, especially human hair, in particular blonde, consisting in the administration of a cosmetic composition as defined in one of embodiments 6 to 10.

22. A cosmetic treatment method intended for dyeing keratin fibres, especially human hair, in particular blonde, consisting in the administration of a cosmetic composition as defined in one of embodiments 14 to 18.

23. A method for dyeing keratin fibres, in particular hair, and more particularly for dyeing hair blonde, comprising the steps:
 a) application of a cosmetic composition comprising a *Gardenia* extract as defined in one of embodiments 1 to 4 or a *Gardenia* powder as defined in one of embodiments 11 to 12,
 b) waiting for a period of time ranging between 15 min and 3 hours,
 c) rinsing with water,
 d) optional repetition of steps a) to c),
 e) optional drying.

24. The dyeing method according to embodiment 23, characterized in that it comprises an optional step, before step a), consisting in the preparation of the composition immediately before use by mixing the components of a kit as defined in one of embodiments 19 or 20 or by mixing a *Gardenia* extract as defined in one of embodiments 1 to 4 with water or by mixing a *Gardenia* powder as defined in one of embodiments 11 to 12 with water.

25. Use of a *Gardenia* extract according to one of embodiments 1 to 5 or use of a composition according to one of embodiments 6 to 10, characterized in that the extract is obtained by a preparation process comprising the following steps:
 extraction from *Gardenia* fruits, in particular from dried fruits, optionally in the presence of pectinases, with a solvent selected from the group consisting of water, ethanol, acetone and mixtures thereof,
 solid-liquid separation,
 optional sterilization of the filtrate, and
 optionally evaporation of the solvent at temperatures below 80° C.

26. Use according to embodiment 25, characterized in that the solvent is selected from the group consisting of water, ethanol and mixtures thereof.

27. Use according to one of embodiments 25 or 26, characterized in that the extraction step is performed at a pH ranging between 4 and 8, preferably between 5 and 7.5, advantageously between 5.5 and 7.5, typically at neutral pH.

The term "dyeing blonde", within the meaning of the present invention, is understood to mean dyeing blonde (No. 7), light blonde (No. 8), very light blonde (No. 9) or platinum blonde (No. 10) as defined as used according to the universal scale (from No. 1 to No. 10) for naming the shade levels used in professional hairstyling.

The present invention stems from a desire to establish synthetic pathways that are greener and that make it possible to lay claim to the natural nature of the active principles thus obtained. Therefore, the one or more solvents used within the context of the present invention will preferably be solvents which are natural and/or of natural origin derived from renewable resources, as opposed to fossil resources, these solvents which may advantageously be obtained by environmentally-friendly processes. The extract thus obtained according to the process of the invention will therefore preferably be an extract which is natural and/or of natural origin, derived from renewable resources, as opposed to fossil resources.

In a preferred embodiment, the process employed makes it possible to preserve the molecules of interest, the crocins, in their native, i.e., glycosylated, form. Dyeing is thus obtained thanks to the pigments naturally present in the plant. Therefore, the process according to the invention does not comprise any step consisting in adding b-glucosidase and/or an amino acid.

A *Gardenia* extract according to the invention can further contain any compound naturally present in *Gardenia* fruits.

In a particular embodiment, an extract according to the invention contains no more than 10%, expressed as weight percent, of geniposide relative to the total weight of the dry extract, in particular between 7 and 10 wt %. When speaking about the total weight of the dry extract, it is the dry extract of *Gardenia*, save for a possible maltodextrin-type neutral support, for example.

The *Gardenia* extract according to the invention can be an aqueous or alcoholic or hydroalcoholic extract.

The *Gardenia* extract according to the invention can be in a liquid or fluid form, i.e., all or part of the extraction solvent is still present.

The *Gardenia* extract according to the invention can be in the form of a dry extract, i.e., the extraction solvent has been removed, for example evaporated, in order to obtain a dry extract.

The *Gardenia* extract according to the invention is water-miscible or -soluble, depending on whether it is a liquid extract or a dry extract, respectively. According to the amount of water added, the extract obtained can thus be in the form of a solution which is liquid, fluid, or more or less viscous.

The *Gardenia* extract according to the invention may be a fluid or pasty, aqueous or hydroalcoholic extract. It can be a dry, aqueous or hydroalcoholic extract. In particular it is an aqueous extract.

The present invention relates to the use of a cosmetic composition intended for dyeing keratin fibres, especially human, said cosmetic composition comprising as active principle a *Gardenia* extract, extracted as described above.

According to a particular embodiment, the use of the cosmetic composition is directed at the dyeing of hair, in particular the dyeing of hair blonde. More particularly, the invention is directed at the dyeing blonde of hair which has been bleached beforehand.

In another embodiment, the invention is directed at the use of a cosmetic composition intended for dyeing keratin fibres, especially human, said cosmetic composition comprising as active principle a fluid extract of *Gardenia*.

In another embodiment, the invention is directed at the use of a cosmetic composition intended for dyeing keratin fibres, especially human, said cosmetic composition comprising as active principle a dry extract of *Gardenia*.

According to a particular embodiment of the invention, a fluid or liquid extract of *Gardenia*, more particularly an aqueous or hydroalcoholic extract of *Gardenia*, according to the invention can thus be in the form of the liquid or fluid fraction (more or less viscous) obtained after liquid-solid extraction and separation and containing from 20 to 60 wt % *Gardenia* dry matter, thus representing the dry extract, and more particularly containing from 30 to 50 wt % *Gardenia* dry matter, thus representing the dry extract, and even more particularly containing about 40 wt % *Gardenia* dry matter, thus representing the dry extract in the aqueous or hydroalcoholic solvent. The extraction is performed on *Gardenia* fruits by known techniques which are detailed below.

According to another particular embodiment of the invention, the extract according to the invention can also be in the form of dry extract once the aqueous or hydroalcoholic solvent is removed, for example by evaporation, from the fluid or liquid extract. This dry extract is typically pulverulent having an average particle size ranging between 0.1 µm and 250 µm, particularly between 1 µm and 250 µm.

The term "dry extract", within the meaning of the present invention, is intended to mean an extract free of extraction solvent, or containing only an insignificant trace amount thereof. Such a dry extract thus contains only the material derived from *Gardenia*, in particular *Gardenia* fruits.

The cosmetic composition according to the invention thus comprises, in addition to the *Gardenia* extract as defined above as dye active principle, a cosmetically acceptable excipient.

The cosmetic composition according to the invention has a pH ranging between 4 and 8, preferably between 5 and 7.5, advantageously between 5.5 and 7.5, typically a neutral pH. The term "neutral pH" is intended to mean a pH ranging between 6.5 and 7.5, particularly around 7.

The composition according to the invention is in particular free of thiol-type reducing compound, for example.

The composition according to the invention is in particular free of ammonia-type alkaline fixing compound, for example.

It is indeed a great advantage and a particularly advantageous feature of the compositions according to the invention to be functional, i.e., to allow powerful, long-lasting dyeing while being free of additives of the reducing or alkaline fixing agent type usually encountered in the dye formulations of the prior art.

It is known that these additives can affect the long-term integrity of the fibre and irritate the scalp. The extracts and compositions according to the invention thus allow rapid, effective and long-lasting dyeing without incurring the problems associated with the presence of these fixing or reducing compounds. The dyeing method thus proposed according to the invention makes it possible to dye the hair fibre while preserving its integrity and its natural state.

The term "cosmetically acceptable excipient", within the meaning of the present invention, is intended to mean an excipient containing ingredients suited to the formulation of cosmetic compositions of cream, lotion, shampoo, emulsion type or any formulation suitable for application to the hair and the scalp.

The invention is also directed at the use of a *Gardenia* powder, more particularly a powder of *Gardenia* fruit, in particular dried fruits, for dyeing hair, in particular for dyeing hair blonde. More particularly, the invention is directed at the dyeing blonde of hair which has been bleached beforehand.

In a particular embodiment, the term "*Gardenia* powder" is intended to mean a pure natural product derived from *Gardenia* fruits, in particular dried fruits, reduced, by grinding or other mechanical means, to fine particles having an average particle size ranging between 0.1 µm and 250 µm, particularly between 1 µm and 250 µm. The grinding of said *Gardenia* fruits in order to obtain a powder can advantageously be performed by grinding the dried fruits by any suitable means allowing a reduction of size and the production of fine particles as mentioned above.

In a preferred embodiment, a powder according to the invention is a dry and pulverulent product whose moisture content is negligible.

A powder according to the invention is thus water-soluble, i.e., it can be used to obtain an aqueous or hydroalcoholic liquid composition containing 20 to 60 wt % dry matter, more particularly between 30 and 50 wt % dry matter, and even more particularly about 40 wt % dry matter. The dry matter thus represents the *Gardenia* powder.

A powder according to the invention can further contain any compound naturally present in *Gardenia* fruits.

In a particular embodiment, a *Gardenia* powder according to the invention contains no more than 10%, expressed as weight percent, of geniposide, relative to the total weight of the *Gardenia* powder, in particular between 1 and 5 wt %.

The term "keratin fibres" is intended to mean head hair, body hair, lashes, eyebrows, more particularly head hair.

In another embodiment, the invention is directed at the use of a cosmetic composition intended for dyeing keratin fibres, especially human, said cosmetic composition comprising as active principle a *Gardenia* powder as defined above. More particularly, the invention is directed at the dyeing blonde of hair which may be bleached beforehand.

In particular, the invention is directed at the use of a cosmetic composition intended for dyeing keratin fibres, especially human, said cosmetic composition comprising as active principle a *Gardenia* powder. In particular, the use according to the invention is directed at the dyeing of hair blonde. More particularly, the invention is directed at the dyeing blonde of hair which has been bleached beforehand.

The cosmetic composition according to the invention thus comprises, in addition to the *Gardenia* powder as defined above as dye active principle, a cosmetically acceptable excipient.

The composition according to the invention is in particular free of thiol-type reducing compound, for example.

The composition according to the invention is in particular free of ammonia-type alkaline fixing compound, for example.

It is indeed a great advantage and a particularly advantageous feature of the compositions according to the invention to be functional, i.e., to allow powerful, long-lasting dyeing while being free of additives of the reducing or alkaline fixing agent type usually encountered in the dye formulations of the prior art.

It is known that these additives can affect the long-term integrity of the fibre and irritate the scalp. The powders and compositions according to the invention thus allow rapid, effective and long-lasting dyeing without incurring the problems associated with the presence of these fixing or reducing compounds. The dyeing method thus proposed according to the invention makes it possible to dye the hair fibre while preserving its integrity and its natural state.

Preferably, the *Gardenia* extract comes from the species *Gardenia jasminoides*, and more preferentially the species *Gardenia jasminoides* var. *radicans*. This variety is particularly rich in crocins.

Also, preferably, the *Gardenia* powder can come from *Gardenia jasminoides*, and more preferentially the species *Gardenia jasminoides* var. *radicans*. This variety is particularly rich in crocins.

According to an embodiment of the invention, the *Gardenia* extract or powder used for dyeing keratin fibres, in particular hair, contains, expressed as weight percent, between 0.1 and 10% crocins, preferentially between 1 and 5%, relative to the weight of the dry extract or the powder.

In a preferred embodiment, the *Gardenia* extract or powder according to the invention is used for dyeing keratin fibres, in particular hair, blonde. More particularly, the invention is directed at the dyeing blonde of hair which has been bleached beforehand.

The composition according to the invention can be formulated for administration to humans. The compositions according to the invention can be administered via the topical route to keratin fibres. Advantageously, the composition according to the present invention is intended for administration via the topical route.

According to a particularly advantageous embodiment of the invention, the cosmetic composition comprises at least one cosmetically acceptable excipient, in particular a viscosifying excipient.

In the present invention, the term "cosmetically acceptable" is intended to mean that which is useful in the preparation of a cosmetic composition, which is generally safe, nontoxic and neither biologically nor otherwise undesirable and which is acceptable for cosmetic use, in particular by topical application to the hair and the scalp.

The compositions according to the invention are advantageously intended for topical application, in particular to the hair and the scalp.

In the latter case, the *Gardenia* extract can be administered in unit dosage forms, mixed with water or conventional cosmetic supports, in particular viscosifying agents, suitable for humans. The suitable unit dosage forms include the forms via the topical route.

If *Gardenia* powder is used, it can be administered in unit dosage forms, mixed with water or conventional cosmetic supports, in particular viscosifying agents, suitable for humans. The suitable unit dosage forms include the forms via the topical route.

Thus, according to an embodiment, the invention relates to a kit comprising a *Gardenia* extract according to the invention, a cosmetically acceptable excipient and a set of instructions, for use for dyeing hair, in particular for dyeing hair blonde. In a particular case, the cosmetically acceptable excipient can be water.

Thus, according to an embodiment, the invention relates to a kit comprising a *Gardenia* powder according to the invention, a cosmetically acceptable excipient and a set of instructions, for use for dyeing hair, in particular for dyeing hair blonde. In a particular case, the cosmetically acceptable excipient can be water.

In a particular embodiment of the invention, the composition comprises, per unit dose, from 10 mg to 100 g of dry extract of *Gardenia* or of *Gardenia* powder, preferentially from 20 mg to 100 g, advantageously from 50 mg to 100 g and more preferentially from 100 mg to 100 g, even more particularly from 200 mg to 75 g.

In a particular embodiment of the invention, the composition comprises, per unit dose, from 0.2 mg to 5 g of crocins, preferentially from 1 mg to 5 g and more preferentially from 2 mg to 2 g.

According to an embodiment of the invention, the *Gardenia* extract or powder contains, expressed as weight percent relative to the dry weight of the extract (save for drying aid) or of the powder, between 0.1 and 10% crocins, preferentially between 0.5 and 8%, preferably between 1 and 5%, even more preferentially between 1 and 3%.

According to a particularly advantageous embodiment of the invention, the cosmetic composition further comprises at least one other dyeing agent, in particular derived from plants, from microorganisms or from microalgae.

The present invention also relates to a cosmetic treatment method intended for dyeing keratin fibres, especially human hair, in particular blonde, consisting in the administration of a cosmetic composition comprising a *Gardenia* extract according to the invention. Preferably, the administration consists of topical application to the hair and the scalp. More particularly, the invention is directed at the dyeing blonde of hair which has been bleached beforehand.

The present invention further relates to a cosmetic treatment method intended for dyeing keratin fibres, especially human hair, in particular blonde, consisting in the administration of a cosmetic composition comprising the *Gardenia* powder according to the invention. Preferably, the administration consists of topical application to the hair and the scalp. More particularly, the invention is directed at the dyeing blonde of hair which has been bleached beforehand.

According to a particular embodiment, the invention is also directed at a method for dyeing keratin fibres, in particular hair, and more particularly for dyeing hair blonde, comprising the steps:
a). application of a cosmetic composition comprising a *Gardenia* extract or powder according to the invention,
b). waiting for a period of time ranging between 15 min and 3 hours,
c). rinsing with water,
d). optional repetition of steps a) to c),
e). optional drying.

According to an embodiment, the method for dyeing keratin fibres according to the invention, in particular hair, and more particularly for dyeing hair blonde, can comprise an optional step, before step a), consisting in the preparation of a composition immediately before use by mixing the components of a kit which comprises a *Gardenia* extract according to the invention and a cosmetically acceptable excipient for use for dyeing hair.

Lastly, the method for dyeing keratin fibres, in particular hair, and more particularly for dyeing hair blonde, can comprise an optional step, before step a), consisting in the preparation of a composition immediately before use by mixing the components of a kit which comprises a *Gardenia* powder according to the invention and a cosmetically acceptable excipient for use for dyeing hair. A composition can be prepared just as easily by mixing the powder with water or by mixing the extract with water.

Waiting step b) can advantageously be performed at a temperature ranging between 30° C. and 100° C. (for example using a bonnet hair dryer), more particularly between 30° C. and 75° C., even more particularly around 40° C. to 60° C., and still more particularly around 50° C.

More particularly, the invention is directed at a method for the dyeing blonde of hair which has been bleached beforehand.

The hair dyeing method according to the invention can comprise repeated application of the cosmetic composition according to the invention.

The hair dyeing method may comprise a rinsing step between the repeated applications of the cosmetic composition according to the invention.

In a particular embodiment, the dyeing process according to the invention does not comprise any step consisting in varying the pH of the composition by adding acid or base before application to the hair.

In particular, the dyeing process is performed at a pH ranging between 4 and 8, preferably between 5 and 7.5, advantageously between 5.5 and 7.5, typically at neutral pH.

The term "neutral pH" is intended to mean a pH ranging between 6.5 and 7.5, particularly around 7.

Likewise, it is not necessary to apply a fixing compound (ammonia-type alkali) or reducing compound (for example thiol).

Finally, the present invention relates to a method of preparation of extract of *Gardenia*, particularly of *Gardenia* fruits.

In an embodiment of the invention, the *Gardenia* extract is obtained by:
extraction with aqueous, organic or hydroalcoholic solvent from whole fruits, optionally in the presence of pectinases,
solid-liquid separation,
optional sterilization of the filtrate, and
optionally evaporation of the solvent at temperatures below 80° C.

The *Gardenia* fruits are extracted with a solvent selected from the group consisting of water, an organic solvent such as ethanol, or acetone, and mixtures thereof. Extraction can be performed on whole fruits or on fruits coarsely ground beforehand. Enzymes, such as pectinases, can be added in order to improve the extraction and/or the filtration thereof by fluidifying the extraction juices. The process is particularly characterized by the absence of glycosidase in order to avoid the formation of crocetin. Extraction can be performed by a conventional method known to persons skilled in the art, in a reactor, by ultrasound or by microwaves at a temperature ranging between 20° C. and 100° C. depending on whether enzymes are present. Extraction can be performed at atmospheric pressure or under pressure with subcritical water.

After solid-liquid separation, the liquid fraction (i.e., the filtrate) can be concentrated, sterilized and can be dried as such or on a drying aid, such as maltodextrin or silica. Drying is performed at temperatures below 80° C. in order to avoid degradation of the crocins, molecules which are unstable at higher temperatures. It can be performed by techniques known to persons skilled in the art, for instance by microwaves, lyophilization or spraying.

According to a preferred embodiment, the process according to the invention does not comprise any step consisting in varying the pH of the aqueous solution by adding acid or base.

In particular, the extraction step is performed at a pH ranging between 4 and 8, preferably between 5 and 7.5, advantageously between 5.5 and 7.5, typically at neutral pH.

The term "neutral pH" is intended to mean a pH ranging between 6.5 and 7.5, particularly around 7.

The following examples illustrate the invention without limiting the scope thereof.

Example 1: Preparation of the *Gardenia* Extract

Whole *Gardenia* fruits are extracted with water at 90° C. for 2 hours. After solid/liquid separation, pectinases are added. The filtrate is concentrated on water qs 40% dry extract, sterilized then dried with microwaves.

The dry extract obtained is a red powder. The yield is about 25%. The crocins contents are between 0.1 and 10 wt % of the dry extract, the average crocins content is about 2%.

The *Gardenia* fruits are extracted with water preferentially or a mixture of water and an organic solvent, an alcohol such as ethanol or a ketone such as acetone. Extraction can be performed on whole fruits or on fruits coarsely ground beforehand. Enzymes, such as pectinases, can be added in order to improve filtration. Extraction can be performed by a conventional method known to persons skilled in the art, in a reactor, by ultrasound or with subcritical water or by microwaves at a temperature ranging between 20° C. and 100° C. depending on whether enzymes are present. After solid-liquid separation, the filtrate is used as such or concentrated preferably to 2 volumes of water for 1 part of plant employed, and is preferably sterilized. It can then be dried as such (i.e., without drying aid) by the conventional methods (pallet drying, lyophilization or microwaves or spraying) or on a drying aid, such as maltodextrin or silica. The use of maltodextrin produces better workability. The dry aqueous extract thus obtained is a red powder. The yield is about 25%. The production of 1 kg of extract requires the use of 4 kg of Gardenia fruits. The crocins contents are between 0.1 to 10 wt % relative to the dry extract, the average crocins content is about 2%. Since these molecules are heat-sensitive, the drying temperature is preferentially below 80° C.

Example 2: *Gardenia* Fruits and/or *Gardenia* Fruit Powder

Dried *Gardenia* fruits are used as such or ground with a particle size smaller than 250 µm preferentially.

Example 3: Demonstration of Dyeing Effectiveness on Bleached Human Hair

Dye Composition 1:
The *Gardenia* extract according to Example 1 is mixed with water (mass ratio 1/20 to 1/10 preferentially) at 50° C. or a viscosifying agent such as natural mucilages (xanthan gum, ispaghula, flax, gumbo, konjac, hibiscus, calendula, banana, baobab, acanthus, aloes, etc.).
Process for Dyeing a Lock of Hair Bleached Beforehand (Reference Lock):
The entire lock is dipped in this viscous solution and then placed at 50° C. for 30 min. The lock is then rinsed with hot water.
Dye Composition 2:
The *Gardenia* fruit powder ground with a particle size smaller than 250 µm preferentially is mixed with water (mass ratio 1/20 to 1/10 preferentially) at 50° C. or a viscosifying agent such as natural mucilages (xanthan gum, ispaghula, flax, gumbo, konjac, hibiscus, calendula, banana, baobab, acanthus, aloes, etc.).
Process for Dyeing a Lock of Hair Bleached Beforehand (Reference Lock):
The entire lock is dipped in this viscous solution and then placed at 50° C. for 30 min. The lock is then rinsed with hot water.
Results:
The treated locks are dyed a blonde the intensity (from light blonde to platinum blonde) and the depth of which vary according to the duration and the number of applications relative to the reference lock.
The examples executed above with locks of hair bleached beforehand were reproduced with virgin locks, not bleached beforehand, and the results obtained are in all particulars comparable in terms of the quality and the persistence of the dyeing.

Counter-Example: Geniposide

Preparation of a composition comprising 10 mg of geniposide (supplier: Sigma Aldrich) diluted to 2% in 1 g of xanthan gum.
Process for Dyeing a Lock of Hair Bleached Beforehand (Reference Lock):
The entire lock is dipped in this viscous solution and then placed at 50° C. for 30 min. The lock is then rinsed with hot water.
Result: we observe no dyeing effect compared to the reference lock.

Counter-Example: Crocetin

Crocetin is obtained from the aqueous extract of *Gardenia*, which has been hydrolysed by acid hydrolysis and then purified by chromatography.
Preparation of a composition comprising 10 mg of crocetin diluted to 2% in 1 g of xanthan gum.
Process for Dyeing a Lock of Hair Bleached Beforehand (Reference Lock):
The entire lock is dipped in this viscous solution and then placed at 50° C. for 30 min. The lock is then rinsed with hot water.
Result: we observe no dyeing effect in comparison with the reference lock.

Counter-Example: *Gardenia* Blue

Preparation of a composition comprising 0.5 g of *Gardenia* Blue (E600764 *Gardenia* Blue; supplier: JIANGXI TIANSHUN ECOLOGICAL AGRICULTURE CO) diluted to 2% in 12 g of xanthan gum.
Process for Dyeing a Lock of Hair Bleached Beforehand (Reference Lock):
The entire lock is dipped in this viscous solution and then placed at 50° C. for 30 min. The lock is then rinsed with hot water.
Result: we observe no dyeing effect in comparison with the reference lock.

The invention claimed is:
1. A cosmetic treatment for dyeing keratin fibres, which comprises
   a) contacting said fibres with a cosmetic composition comprising as active principle a *Gardenia* extract comprising between 0.1 and 10 wt % crocins, relative to the weight of the dry extract
   b) waiting for a period of time ranging between 15 min and 3 hours,
   c) rinsing with water,
   d) optional repetition of steps a) to c),
   e) optional drying,
   wherein the cosmetic composition comprises, in addition to the *Gardenia* extract as dye active principle, a cosmetically acceptable excipient,
   wherein the cosmetic composition has a pH ranging between 4 and 8,
   wherein the cosmetic composition is free of reducing compound and wherein the cosmetic composition is free of alkaline fixing compound.
2. A cosmetic treatment for dyeing keratin fibres, which comprises
   a) contacting said fibers with a cosmetic composition comprising as active principle a *Gardenia* powder comprising between 0.1 and 10 wt % crocins relative to the weight of the powder,
   b) waiting for a period of time ranging between 15 min and 3 hours,
   c) rinsing with water,
   d) optional repetition of steps a) to c),
   e) optional rinsing;

wherein the cosmetic composition comprises, in addition to the *Gardenia* powder as dye active principle, a cosmetically acceptable excipient, wherein the cosmetic composition has a pH ranging between 4 and 8, wherein the cosmetic composition is free of reducing compound and wherein the cosmetic composition is free of alkaline fixing compound.

3. A method of dyeing keratin fibres, which comprises
a) contacting said fibres with a *Gardenia* extract comprising between 0.1 and 10 wt % crocins relative to the weight of the dry extract
b) waiting for a period of time ranging between 15 min and 3 hours,
c) rinsing with water,
d) optional repetition of steps a) to c),
e) optional drying, wherein the extract is obtained by a preparation process comprising the following steps:
extraction from *Gardenia* fruits, optionally in the presence of pectinases, with a solvent selected from the group consisting of water, ethanol, acetone and mixtures thereof,
solid-liquid separation,
optional sterilization of the filtrate, and
optionally evaporation of the solvent at temperatures below 80° C., wherein the extraction step is performed at a pH ranging between 4 and 8.

4. The cosmetic treatment according to claim 1 wherein the extract is an extract of *Gardenia* fruits.

5. The cosmetic treatment according to claim 1, wherein the extract is an aqueous or alcoholic or hydroalcoholic extract.

6. The cosmetic treatment according to claim 1, wherein the extract is a dry extract.

7. The cosmetic treatment according to claim 1, wherein the cosmetic composition further comprises at least one other dyeing derived from plants, microorganisms or microalgae.

8. The cosmetic treatment according to claim 2, wherein it comprises an optional step, before step a), comprising the mixing of the *Gardenia* powder with water immediately before use.

9. The cosmetic treatment according to claim 2, wherein the cosmetic composition further comprises at least one other dyeing derived from plants, microorganisms or microalgae.

10. The method according to claim 3, wherein the solvent is selected from the group consisting of water, ethanol and mixtures thereof.

* * * * *